United States Patent [19]

Bonadio

[11] Patent Number: 6,007,847

[45] Date of Patent: Dec. 28, 1999

[54] METHODS FOR ADMINISTERING NUTRITIONAL INDIUM

[76] Inventor: George A. H. Bonadio, 373 E. Ave., Watertown, N.Y. 13601-3829

[21] Appl. No.: 09/021,212

[22] Filed: Feb. 10, 1998

Related U.S. Application Data

[63] Continuation-in-part of application No. 08/802,777, Feb. 18, 1997, abandoned.

[51] Int. Cl.⁶ .......................... A61K 33/24; A61K 31/28
[52] U.S. Cl. ............................................ 424/650; 514/492
[58] Field of Search ............................ 424/650; 514/492, 514/905; 426/74

[56] References Cited

U.S. PATENT DOCUMENTS

| | | | |
|---|---|---|---|
| 3,937,806 | 2/1976 | Cooley | 424/52 |
| 4,182,754 | 1/1980 | Bonadio | 424/650 |
| 4,359,477 | 11/1982 | Rogers | 424/287 |
| 4,591,506 | 5/1986 | Bonadio | 424/131 |
| 5,763,480 | 6/1998 | Schlesinger | 514/476 |

OTHER PUBLICATIONS

Remington's Pharmaceutical Sciences, Joseph Price Remington, 1980; pp. 973–977.

Drug Facts and Comparisons, Facts and Comparisons, 1991–92, 1998; pp. 10f–11; 12b–12c; 15–16; 14–14a; 14a; 17–17a; 12–12–12a; and 13b–13c.

*Primary Examiner*—John Pak
*Attorney, Agent, or Firm*—Trapani & Molldrem

[57] ABSTRACT

A method of administering a Generally Accepted As Safe (GRAS) indium compound, preferably indium sulfate mixed with distilled water, comprises preferably spraying 1 to 27 mg of indium sulfate into the mouth on arising in the morning and without eating or drinking for at least 10 minutes thereafter.

22 Claims, No Drawings

METHODS FOR ADMINISTERING NUTRITIONAL INDIUM

RELATED APPLICATION

This application is a continuation-in-part application partly based on Ser. No. 08/802,777 filed Feb. 18, 1997, now abandoned.

FIELD OF THE INVENTION

The present invention relates to human nutritional supplements and more particularly to methods of administering indium as a mineral nutritional supplement to improve its absorption.

BACKGROUND OF THE INVENTION

The present invention involves improved methods for using the element indium, in the water soluble compound indium sulfate, as a nutritional supplement. Indium is element number 49 in the periodic table of elements. Indium is a "trace element" as it occurs in tiny amounts in nature. It is found in the earth's crust in 0.05 parts per million. The Merck Index (Twelfth Edition) lists eleven indium compounds, nine have industrial uses, but there is no use (nutritional or medical or other) listed for indium sulfate. The Merck Index lists the indium compounds of indium antimonide, indium arsenide, indium gallium aluminum phosphide, indium phosphide, indium selenide, indium telluride, as being used in semiconductors and indium oxide and indium trichloride, as used for other industrial products. However, no indium compound is indicated as being used in a nutritional product.

The term indium, as used hereafter, means elemental indium and its FDA GRAS (Generally Accepted As Safe) compounds. The inventor is not aware of any scientific studies of the effect of indium, used as a nutritional supplement, on people. Indium always occurs in nature as a compound. The only indium compound presently on the FDA "GRAS" (Generally Accepted As Safe) list is indium sulfate.

The present inventor has discovered that indium as a nutritional supplement presents unusual difficulties because of the problem of its non-absorption. Generally nutritional supplements are taken in pill or liquid form. They may be taken at any time of the day and may be taken with food at mealtimes. However, indium sulfate (and it is believed any GRAS approved indium compounds) are poorly absorbed when taken orally.

A scientific study of the effect of indium on animals is an early work by Dr. Henry Schroeder, who is famous for his work on removing lead from gasoline. He studied seven trace elements and their toxic effect on mice (not humans); Schroeder et al, *J.Nutrition*, Vol. 101: 1431-1438 (1971); and Schroeder and Nason, *J.Nutrition*, "Interactions of Trace Metals in Mouse and Rat Tissues; Zinc, Chromium, Copper and Manganese With 13 Other Elements." He concluded that "Indium is not carcinogenic" and it is "relatively not toxic orally". (Schroeder and Mitchener at pages 1435,1436). There is no indication that Dr. Schroeder recognized any health benefits for mice, or for humans, from using indium as a nutritional supplement or that he used indium sulfate in his experiments on mice.

Cooley U.S. Pat. No. 3,937,806 is entitled "Oral Composition For Caries Prophylaxes" and relates to "dentifrices and mouthwashes." They are not swallowed, i.e., "is not intentionally ingested" (col. 1, line 26). It discloses the combination of a "water-soluble fluoride salt and indium-malic acid water soluble complex" (col. 2, lines 22,23). Indium sulfate is not used in the examples. Indium occurs, in trace amounts, in some foods, Zhang et al, "The nutritional components of Actinidia" *Chem. Abstracts*, Vol. 116, No. 37, 847 (1992) which refers to A. Kolomita—(Kiwi fruit) and mentions "Indium, biological studies 7664-41-7", which is a number referring to a Chemical Abstract and is not the amount of indium in Kiwi fruit.

SUMMARY OF THE INVENTION

The present invention is the use of indium sulfate, in a specific range and administered in a certain way as a nutritional supplement.

Indium sulfate is the only indium compound presently listed as Generally Recognized As Safe (GRAS list) by the FDA. The Index Medicus, MEDLINE (National Cancer Institute) indicates that the toxicity for rabbits (Lethal Dose Lowest—LDC, oral) was 1,300 mg/kg a day and rats 1,200 mg/kg. That dosage is about 20,000 times the usage (on a weight basis) of the nutritional supplement of the present invention. Indium appears in food substantially only as a complex trace contaminant which is not usable nutritionally.

Indium sulfate is hygroscopic, so that in pills, capsules and tablets it eventually ruins those packagings, each molecule of sulfate taking on nine molecules of water. It should be delivered in a liquid form.

When indium sulfate is taken orally, it makes contact with other food in the upper digestive tract. It readily mixes with the other food and ceases being useful to the body. Consequently, there is little absorption by the body.

The method of the present invention requires the user not to take indium with, or after, any other food product, which may be in the upper digestive tract, above the intestines. Some foods take over seven hours to completely clear out of the stomach.

The best time for administering indium sulfate is upon arising, and before any food or drink. The typically active person needs at least 10 minutes, or more, to absorb most of the indium, without being complexed with food. An inactive bedridden invalid should extend that time to at least 30 minutes.

The administration is with water which is preferably distilled. Other waters can contain enough other elements to destroy the benefits of the indium compound. A day's supply is preferably about 10 milligrams of indium sulfate in a drop of water weighing 60 milligrams. A preferred ratio is about 2.25 mg of the sulfate, which holds one milligram of indium metal, in one drop, providing user convenience of varying his intake by the number of drops.

Some absorption is likely in the mouth and in the stomach. Almost none is apt to reach the intestines.

Experiments proved that contact of indium sulfate with food often eliminated the benefits which come from good body absorption of indium. There are many chemical compounds in foods present in the upper digestive tract and these make the indium unavailable for body absorption.

Absorption of indium is greatly improved by avoiding food or drink in the upper digestive tract (to the end of the stomach) and avoiding impurities in the water carrier.

It is an important feature of the present invention that the indium compound, preferably indium sulfate, be absorbed by being taken orally. This involves various techniques: (i) the indium compound should be taken at the right time. That time is in the morning prior to eating or drinking; e.g., on an empty stomach, and waiting at least 10 minutes before eating or drinking; (ii) the indium compound should be administered by spraying into the mouth and which is preferable to pills or liquid; (iii) the indium compound should be carried by the minimum amount of water, which is accomplished by mixing in a ratio of 1 indium compound to the range of 0.4–50 water (by weight) and most preferably indium sulfate is at least 0.0001% of the mixture (by weight).

The indium sulfate is dissolved into distilled water and is preferably administered by an oral spray (a spray into the mouth), using a spray pump, to overcome its high surface tension. It is used at least twice a week. Preferably the concentration of indium (not indium sulfate) is 1 mg per spray or per drop of liquid.

The range of the amount of indium sulfate (not the diluted solution) which should be taken is from 0.016 mg to 0.16 mg per pound of the user's weight. Another way to express this is in terms of ppm (parts per million) of body weight. The preferred amount is about 0.06 ppm per day for each pound of body weight and the preferred range is 0.005 to 0.5 ppm per pound. For an average weight of 154 pounds (70 kg) this is 154×0.06 ppm or is about 4 mg per day of indium. Indium is 44.35% of indium sulfate (by weight). Except for persons of extreme weight lightness or heaviness, this is an amount of 0.27 mg to 27 mg per intake, the average per day. The most preferred amount is 1 mg per 33 lbs. of body weight and the dosage should be used at least twice per week.

DETAILED DESCRIPTION OF THE INVENTION

Indium Sulfate Carrier

It is important that the surface tension of the indium sulfate, which comes as a liquid, be lowered and that it be broken into small droplets by spraying. The preferred carriers are (1) distilled water, (2) alcohol, (3) water and cane sugar, (4) a weak liquid acid such as acetic acid, citric acid, alcohol, and vinegar. In addition, a suitable emulsifier and a chelating agent may be added to the mixture.

The most preferred mixture, which is adapted to be sprayed from a spray bottle, is as follows: indium sulfate 1 kg (2.2 lbs) (99.9% purity) and 1 gallon distilled water. A less pure quality is preferred (99.4%) for cost reasons. A less preferred embodiment is indium sulfate and distilled water and sugar. One kilogram (2.2 lbs) of indium sulfate anhydrous is mixed with one gallon of distilled water and 12 ounces of sugar. These mixtures do not require refrigeration or other special storage.

Indium Sulfate—Recommended Usage

The general preferred amount for oral intake, by humans and domesticated animals, is about one milligram of element indium metal, or 2.25 mg of the sulfate, per 33 pounds of body weight, taken as indium sulfate, mixed in distilled water.

The toxic level of intake or indium sulfate is over 1,000 times this amount. A whole bottle contains an insufficient amount to poison a person to death. Gross excess would probably produce vomiting from the strong taste. It is among the safest of trace elements in nutrition.

The reduction to a single milligram of indium, in each drop, for ease of control of amounts, has thinned the taste to be tolerated by practically everyone. Persons who reject the tart metallic taste of the mixture may be supplied with a lozenge mixture of cane sugar and with a sufficient amount of indium. The user should allow about a half hour after intake, before eating or drinking, due to the bulk and slowness of dissolving of such lozenge. In a hospital medicines are frequently given by nurses before breakfast. The indium should be taken before medicine and with a 30-minute delay, before food intake because the patient's inactivity slows the digestive rates.

Based upon the inventor's experiments, it is recommended that the indium sulfate solution spray be taken 2 or 3 times a week. It should be sprayed into the mouth before breakfast, e.g., on an empty stomach. Food and drink should be avoided for at least 10 minutes. Alternatively, and less desirable, indium sulfate should be taken after six hours without eating or drinking.

This spray method reduces the cost of the indium sulfate to the customer, as it is a rare and expensive material. More importantly, it reduces the surface tension and permits absorption by the user's body. In addition, it avoids indium's metallic taste which some people do not like.

The recommended range of the indium sulfate (not the mixture) is from 0.002 mg/kg to 0.7 mg/kg a day. Based on an average body weight of 70 kg the recommended range of the indium sulfate nutritional supplement is from 0.14 to 0.49 mg.

A GRAS indium compound may be administered to a user by delivering the indium compound in amounts for an optimum intake for the weight of the user and at least 0.27 mg, for each day of usage. The indium compound is mixed with a minimum of carrier to form a mixture. The mixture is administered to the user upon the user arising and the user having an empty stomach. The user should avoid any other nutrition and medicine for at least 10 minutes, thereby allowing substantially full absorption of the indium compound.

A GRAS indium compound may be administered at a daily average amount in the range of 0.005 to 0,5 ppm of the body weight of a human user.

In spray form one spray equals 2.25 mg of indium sulfate in solution. Generally a person should start at one spray a day for 2 or 3 days per week. The amount may be increased, up to 10 sprays per day, until the optimum effects are felt. The amount of indium sulfate solution which is ideal for the individual may vary depending on the person's diet, weight, age and other factors. The inventor suggests three tests to determine the sufficiency of the amount. These tests are (1) improvement in mood for one week or more. Then the indium sulfate is stopped. If the elevated mood disappears in less than 3 days, the amount is insufficient; but if it persists for over 5 days the amount is excessive; (2) long term use (over 1 month). If an excess of new red capillaries on the skin, the amount is excessive; (3) the size of the visible bowel movement, at the correct amount of indium sulfate, should be about the diameter of the middle finger, e.g., larger than the diameter of the little finger and smaller than the diameter of the thumb.

The National Institute of Environmental Health Sciences, Department of Health, Education and Welfare, sponsored a text in a series TRACE METALS IN THE ENVIRONMENT, Volume 5-INDIUM. In it, on pages 9 and 537, the text indicates that the total intake of indium from foods per person per day is less than 8 micrograms (0.008 mg) and indium is absorbed at about 0.2 ug (0.000,2 mg), an absorption rate of about one part in forty. This invention provides an absorption of about 4 mg., or 20,000 times as much, per person per day.

The human user keeps his bottle on his bedside table. Its label tells the user to take orally only upon arising, and to take a satisfactory amount, by experimenting, without other food or drink for at least the next 10 minutes, while the critical absorption is in process. An invalid or bedridden person or inactive person needs to wait at least 30 minutes, because of their inactivity.

The indium sulfate and water mixture may be administered using a simple inexpensive eyedropper. Preferably the mixture contains 1 mg of indium metal per drop. The user may easily change the amount, for example, from, say, 4 to 5 mg per day. With some loss and some irregularity two days' supply may be taken every other day.

The mixture is preferably in a spray bottle in which, preferably, the average squirt carries 1 mg of indium. That is 2.25 mg of indium sulfate per pumping.

Theory Of Operation

The benefits of indium, and its method of administration, do not depend upon a theory of operation. The theory set forth below is the inventor's present best concept of how the indium provides benefits. However, that theory may be modified by future scientific studies.

Preferably the labeling of the packaging lists the user's reactions to find if they are on a satisfactory level. This is important because the hypophysis-hypothalamus feedback loop complex reaches normal levels, via indium, and generates a sense of well being and the joy of living.

The benefits, it is believed, could be either from particular glands or from the "Master Gland" feedback control system, which controls production of at least 31 hormones. Such production is regulated substantially to normal by the hypophysis-hypothalamus (Master Gland) feedback loop, which responds several times per minute.

Twenty-eight of these hormones have half-lives averaging 30 minutes, and nine average under 10 minutes, indicating that hormone pills are unlikely to be satisfactory.

Benefits of Indium

A number of individuals have been given free samples of indium sulfate and have supplemented their diet, on a daily or 2–3 times a week basis, with that compound material. The following is a brief summary of their reports. This was not a controlled clincial or statistical study; but the unsolicited statements of persons unaffiliated with the inventor. It is not a statement of health benefits which other individuals may obtain from using indium sulfate as a nutrition supplement.
1. J.S. reports his high PSA, due to prostate cancer, declined 75%.
2. A doctor reports that some of his diabetic patients reduced their insulin by 80%.
3. A person with Parkinsons Disease reports improvement in walking and speech—within two weeks.
4. A number of reports on the stabilization of the female monthly cycle (menstrual cycle).
5. A doctor reports on improvements in general health of two patients on wasting diarrhea from HIV/AIDS—after two weeks.
6. A dentist reports on increased gum health.
7. A doctor reports an increase in mental energy.
8. Two reports of an improvement in delivery of babies —more rapid.
9. Reports of lowered and gradual reduction, over months, in eyeball pressure in an older person (over 70) without the use of glaucoma medication.
10. Reduction of physical fatigue in sports (sports performance) —within ten days.
11. Reports of increased mental concentration and physical energy.
12. A report of a decrease in recurrent migraine headaches and headache relief—within hours.

Eyeball pressure goes up from childhood from near 8/8, to teen numbers in the teens, and near 20/20 in senior years. An eye examination involves recording of the eye pressure on the person's record. At 20/20 the doctor is alerted and at 25/25 he prescribes serious medication, which may have side effects, and frequent changes of medication. With enough indium, it has been reported, the numbers come down in a few months by 10% to 35%, into a safer range.

A much faster testing of the benefits of indium is the sense of well being, or joy of living, which arises in less than a week. Upon temporarily discontinuing the indium, that pleasure will disappear after about the fourth day. If it disappears in two days, the indium absorption is not enough. If it lasts as long as six days, some excess indium is being wasted.

When the user habitually awakens spontaneously, without any outward signal, he can record how many hours and minutes of sleep he averages, before he starts indium. With indium he should find that he is sleeping less time, for example, over an hour less time. More than the optimum amount of indium will not further this shortening of sleep time, but less than enough will shorten that time. Persons using an alarm for awakening, on a fixed sleeping schedule, will notice a greater sense of refreshment from that same amount of hours in sleep, using the correct amount of indium.

Persons with extremely high blood pressure, such as over 160, will see it come down with enough indium. Dr. Walter Mertz, co-discoverer of the human need for chromium, explained that chromium helps lower blood pressure, but the absorption of chromium is very poor. It is suggested that, in high blood pressure, both indium upon arising and chromium with a meal will be most effective in reducing excessive blood pressure by about 15 points per month, to below 130. Meanwhile, a too low blood pressure will rise slower, to over 100.

An excessive intake, over a long period of time, may double the capillary small red dots on the surfaces of the trunk. After returning to optimum levels, the excess dots will turn brown and slowly fade away.

Type Two Diabetics, using insulin, may need to adjust their daily insulin because indium can change the need of their measured insulin, starting in the first day. An 80% reduction has been reported in one week. Some have needed no insulin after several weeks on indium. These people are not "cured" by indium. The indium may prompt their glandular complex to send more accurate signals to their pancreas for a better level of insulin. Such diabetics need to keep both indium and insulin handy in case either item runs out. In contrast, of eight Type One diabetics (one in 250 of the population) who tested indium, none reported benefits.

Women in pregnancy are prone to diabetes because they use their insulin in production of the hormone relaxin. Relaxin moves the fetus into the optimum support position, preventing some premature deliveries. Relaxin later also causes the pubic area to become very elastic for a natural full-term delivery. Relaxin is not commercially available. Indium appears to generate these two hormones (relaxin and insulin) in pregnant women.

The strenuous exerciser, who knows when to stop due to muscular pains, should find an increase of 10% additional exercise without pain. The indium helps remove the painful buildup, in humans and animals, by improving the natural removal of lactic acid.

The indicators of the effectiveness of the amounts of indium intake and absorption are return to normal range of libido in both male and female by the second week, family reports that the user is easier to live with by the second week, return of sense of smell in seniors in a week, less sleep needed for recuperation in a week, type two diabetic calculation of needed amount of insulin significantly reduced in two weeks, a relief from piles discomfort in two months, an awareness of a continuous sense of well-being in a week, a reversal from a long term dangerous eyeball pressure increase to downward away from the glaucoma endangerment numbers in three months, and endurance of measured severe physical exertion exceeded in two weeks.

What is claimed is:

1. A method of administering indium sulfate for supplementing human nutrition, comprising the steps of:
   (a) orally administering an amount of indium sulfate to a human upon arising and on an empty stomach, the amount being in the range of about 0.002 mg to about 1.4 mg of indium-sulfate per kilogram of body weight per day; and
   (b) avoiding eating or drinking for at least 10 minutes from the oral administration of the indium sulfate;
   wherein no other supplementary nutritional or dietary ingredient is administered in combination or in admixture with the indium sulfate.

2. The method of claim 1, wherein the indium sulfate is orally administered at least two times per week.

3. The method of claim 1, wherein the amount of indium sulfate is in the range of about 0.002 mg to about 0.7 mg per kilogram of body weight per day.

4. The method of claim 1, wherein said step (a) is performed by orally administering a mixture of the indium sulfate and a carrier.

5. The method of claim 4, wherein said step (a) is performed by dropping the mixture into the mouth.

6. The method of claim 4, wherein said step (a) is performed by spraying the mixture into the mouth.

7. The method of claim 4, wherein the mixture is in the form of a solid lozenge, and wherein said step (a) is performed by dissolving the lozenge in the mouth.

8. The method of claim 4, wherein said carrier is distilled water, and the mixture has a ratio of indium sulfate to distilled water in a range of about 1:0.4 to about 1:50 by weight.

9. The method of claim 8, wherein the mixture has a weight ratio of indium sulfate to distilled water of about 1:6.

10. The method of claim 1, wherein said step (a) is performed by administering a mixture of the indium sulfate and a rapidly absorbed carrier, said carrier being selected from the group consisting of alcohol, cane sugar and water mixture, vinegar, distilled water, acetic acid, and citric acid, whereby the absorption of the indium sulfate into the body is accelerated.

11. The method of claim 1, wherein the indium sulfate is contained within a sugar lozenge.

12. The method of claim 1, wherein said step (b) is performed by avoiding eating or drinking for at least 30 minutes from the oral administration of the indium sulfate.

13. A method of administering indium sulfate for supplementing human nutrition, comprising the steps of:
   (a) orally administering an amount of indium sulfate to a human on an empty stomach, the amount being in the range of about 0.002 mg to about 1.4 mg of indium sulfate per kilogram of body weight per day; and
   (b) avoiding eating or drinking for at least 10 minutes from the oral administration of the indium sulfate;
   wherein no other supplementary nutritional or dietary ingredient is administered in combination or in admixture with the indium sulfate.

14. A method of administering indium sulfate for supplementing human nutrition, comprising the steps of;
   (a) orally administering an amount of indium sulfate to a human after at least six hours without eating or drinking, the amount being in the range of about 0.002 mg to about 1.4 mg of indium sulfate per kilogram of body weight per day; and
   (b) avoiding eating or drinking for at least 10 minutes from the oral administration of the indium sulfate;
   wherein no other supplementary nutritional or dietary ingredient is administered in combination or in admixture with the indium sulfate.

15. A method of administering indium sulfate for supplementing human nutrition, comprising the steps of;
   (a) orally administering a daily average amount of indium sulfate to a human on an empty stomach, the daily average amount being in the range of about 0.005 mg to about 1.0 mg of indium sulfate per kilogram of body weight; and
   (b) avoiding eating or drinking for at least 10 minutes from the oral administration of the indium sulfate;
   wherein no other supplementary nutritional or dietary ingredient is administered in combination or in admixture with the indium sulfate.

16. The method of claim 15, wherein the indium sulfate is orally administered at least two times per week.

17. The method of claim 15, wherein the daily average amount of indium sulfate is in the range of about 0.005 mg to about 0.5 mg per kilogram of body weight per day.

18. The method of claim 15, wherein said step (a) is performed by orally administering a mixture of the indium sulfate and a carrier.

19. The method of claim 18, wherein said step (a) is performed by dropping the mixture into the mouth.

20. The method of claim 18, wherein said step (a) is performed by spraying the mixture into the mouth.

21. The method of claim 18, wherein the mixture is in the form of a solid lozenge, and wherein said step (a) is performed by dissolving the lozenge in the mouth.

22. The method of claim 15, wherein the indium sulfate is contained within a sugar lozenge.

* * * * *